United States Patent
Yanev et al.

(10) Patent No.: US 10,102,345 B2
(45) Date of Patent: Oct. 16, 2018

(54) PERSONAL WELLNESS MANAGEMENT PLATFORM

(75) Inventors: Kostadin Dimitrov Yanev, Alamo, CA (US); Angel Georgiev Vassilev, Sofia (BG); Ivo Kostadinov Yanev, Sofia (BG)

(73) Assignee: ACTIVBODY, INC., Aliso Viejo, CA (US)

(*) Notice: Subject to any disclaimer, the term of this patent is extended or adjusted under 35 U.S.C. 154(b) by 0 days.

(21) Appl. No.: 13/527,401

(22) Filed: Jun. 19, 2012

(65) Prior Publication Data
US 2013/0337974 A1    Dec. 19, 2013

(51) Int. Cl.
*A61N 1/36*    (2006.01)
*G06F 19/00*    (2018.01)
(Continued)

(52) U.S. Cl.
CPC ........ *G06F 19/3481* (2013.01); *A61B 5/0022* (2013.01); *A61B 5/0205* (2013.01);
(Continued)

(58) Field of Classification Search
CPC ........ A63B 2071/0625; A63B 24/0062; A63B 2225/50; A63B 2230/06; A63B 3/0005
(Continued)

(56) References Cited

U.S. PATENT DOCUMENTS 4,577,625 A   3/1986   Lohati et al. .................... 128/57
4,702,108 A   10/1987   Amundsen
(Continued)

FOREIGN PATENT DOCUMENTS

CN    201270095    8/2009
EP    2 284 646    2/2011
(Continued)

OTHER PUBLICATIONS

"Fitness Made Fun", WiiFit, Instruction Booklet, copyright 2008 Nintendo, 28 pages.
(Continued)

*Primary Examiner* — Sundhara Ganesan
(74) *Attorney, Agent, or Firm* — Pillsbury Winthrop Shaw Pittman LLP

(57) ABSTRACT

A personal wellness system may facilitate personal wellness management via personal wellness devices. The personal wellness devices may be portable, handheld devices configured to facilitate personal exercise and personal wellness management using the device. Exercises performed using the personal wellness devices may be tracked based on forces exerted on the personal wellness device, a location and/or motion of the personal wellness device, and/or other bases for tracking personal exercise. Tracked exercises may be a basis for determining exercise parameters such as information associated with cardiovascular endurance, respiratory endurance, stamina, strength, flexibility, power, speed, coordination, agility, and/or balance; calories burnt or energy expended; a completion level of a prescribed exercise routine; a quantified improvement in an exercise; and/or other exercise parameters. The personal wellness system may facilitate automated and/or live coaching, exercise regimen design, exercise scheduling, diet program design, rehabilitation, and/or other functions associated with personal wellness management.

17 Claims, 3 Drawing Sheets

(51) Int. Cl.
  *A61B 5/00* (2006.01)
  *A61B 5/0205* (2006.01)
  *A61B 5/11* (2006.01)
  *A61B 5/024* (2006.01)
  *A61B 5/145* (2006.01)

(52) U.S. Cl.
  CPC ............. *A61B 5/11* (2013.01); *A61B 5/7275* (2013.01); *A61B 5/7455* (2013.01); *A61B 5/024* (2013.01); *A61B 5/1112* (2013.01); *A61B 5/1118* (2013.01); *A61B 5/1123* (2013.01); *A61B 5/14532* (2013.01); *A61B 2505/09* (2013.01); *A61N 1/36003* (2013.01); *F04C 2270/041* (2013.01)

(58) Field of Classification Search
  USPC .................................................. 482/1, 8, 9
  See application file for complete search history.

(56) References Cited

U.S. PATENT DOCUMENTS

| | | | |
|---|---|---|---|
| 4,824,103 A | 4/1989 | Smidt ........................... 272/125 |
| 4,988,981 A | 1/1991 | Zimmerman |
| 5,144,284 A | 9/1992 | Hammett |
| 5,242,348 A | 9/1993 | Bates ........................... 482/105 |
| 5,471,405 A | 11/1995 | Marsh .......................... 364/556 |
| 5,702,323 A | 12/1997 | Poulton |
| 5,720,711 A | 2/1998 | Bond et al. ..................... 601/23 |
| 5,790,102 A | 8/1998 | Nassimi ........................ 345/163 |
| 5,792,080 A | 8/1998 | Ookawa et al. ............. 601/115 |
| 5,890,995 A | 4/1999 | Bobick et al. .................... 482/4 |
| 5,904,639 A | 5/1999 | Smyser et al. ................. 482/91 |
| 5,923,318 A | 7/1999 | Zhai |
| 5,982,342 A | 11/1999 | Iwata |
| 5,997,489 A | 12/1999 | Iwamoto et al. ............... 601/73 |
| 6,013,007 A | 1/2000 | Root et al. ....................... 482/8 |
| 6,063,045 A | 5/2000 | Wax |
| 6,126,572 A | 10/2000 | Smith .............................. 482/4 |
| 6,183,425 B1 | 2/2001 | Whalen et al. ............... 600/592 |
| 6,191,773 B1 | 2/2001 | Maruno |
| 6,222,465 B1 | 4/2001 | Kumar |
| 6,227,968 B1 | 5/2001 | Suzuki et al. .................... 463/7 |
| 6,324,557 B1 | 11/2001 | Chan ............................. 708/142 |
| 6,359,611 B2 | 3/2002 | Chan ............................. 345/156 |
| 6,360,597 B1 | 3/2002 | Hubbard, Jr. ................... 73/172 |
| 6,405,278 B1 | 6/2002 | Liepe ............................ 711/103 |
| 6,435,937 B1 | 8/2002 | Naegele ........................ 446/298 |
| 6,513,532 B2 | 2/2003 | Mault et al. ................... 128/921 |
| 6,585,668 B2 | 7/2003 | Nissim |
| 6,595,901 B2 | 7/2003 | Reinbold et al. ............... 482/91 |
| 6,597,347 B1 | 7/2003 | Yasutake |
| 6,605,038 B1* | 8/2003 | Teller et al. .................. 600/300 |
| 6,616,579 B1 | 9/2003 | Reinbold et al. ............... 482/91 |
| 6,662,651 B1 | 12/2003 | Roth ......................... 73/379.02 |
| 6,675,130 B2 | 1/2004 | Kanevsky et al. ............ 702/188 |
| 6,776,345 B1 | 8/2004 | Liang ........................... 235/486 |
| 6,807,869 B2 | 10/2004 | Farringdon et al. ..... 73/862.046 |
| 6,837,827 B1 | 1/2005 | Lee et al. ......................... 482/8 |
| 6,914,695 B2 | 7/2005 | Walters et al. ............. 358/1.15 |
| 6,956,833 B1 | 10/2005 | Yukie et al. .................. 370/328 |
| 6,975,644 B2 | 12/2005 | Tordera et al. ............... 370/463 |
| 7,026,940 B2 | 4/2006 | Cherubini |
| 7,121,982 B2 | 10/2006 | Feldman |
| 7,161,490 B2 | 1/2007 | Huiban |
| 7,169,120 B2 | 1/2007 | Murdock et al. ............. 601/129 |
| 7,192,387 B2 | 3/2007 | Mendel ............................ 482/8 |
| 7,229,385 B2 | 6/2007 | Freeman et al. .................. 482/4 |
| 7,292,867 B2 | 11/2007 | Werner et al. ............. 455/456.3 |
| 7,303,534 B2 | 12/2007 | Kahn ............................ 600/587 |
| 7,398,151 B1 | 7/2008 | Burrell et al. ................. 701/200 |
| 7,429,251 B2 | 9/2008 | Tanizawa et al. ............... 601/94 |
| 7,468,968 B2 | 12/2008 | Svensson et al. ............. 370/338 |
| 7,480,512 B2 | 1/2009 | Graham et al. ............. 455/456.3 |
| 7,499,746 B2 | 3/2009 | Buhlmann et al. .............. 607/2 |
| 7,517,327 B1 | 4/2009 | Knight ........................... 601/46 |
| 7,526,314 B2 | 4/2009 | Kennedy ................... 455/556.1 |
| 7,526,954 B2 | 5/2009 | Haselhurst et al. ............. 73/172 |
| RE40,891 E | 9/2009 | Yasutake |
| 7,643,895 B2 | 1/2010 | Gupta et al. ..................... 700/94 |
| 7,666,118 B1 | 2/2010 | Anthony |
| 7,699,755 B2 | 4/2010 | Feldman |
| 7,699,757 B2 | 4/2010 | Clem et al. .................... 482/49 |
| 7,702,821 B2 | 4/2010 | Feinberg et al. ............... 710/13 |
| 7,717,825 B2 | 5/2010 | Van Der Hoeven |
| 7,758,469 B2 | 7/2010 | Dyer et al. ....................... 482/4 |
| 7,789,800 B1 | 9/2010 | Watterson et al. .............. 482/8 |
| 7,840,346 B2 | 11/2010 | Huhtala et al. ............... 701/209 |
| 7,909,741 B2 | 3/2011 | Kim |
| 7,975,543 B2 | 7/2011 | Clem et al. ................ 73/379.02 |
| 8,009,056 B2 | 8/2011 | Greene |
| 8,025,606 B2 | 9/2011 | Hamilton |
| 8,027,822 B2 | 9/2011 | Turgiss et al. .................. 703/11 |
| 8,172,723 B1 | 5/2012 | Yanev et al. ..................... 482/8 |
| 8,200,323 B2* | 6/2012 | DiBenedetto et al. ........ 600/519 |
| 8,203,454 B2 | 6/2012 | Knight |
| 8,287,434 B2 | 10/2012 | Zavadsky |
| 8,343,013 B1 | 1/2013 | Yanev et al. ..................... 482/8 |
| 8,491,446 B2 | 7/2013 | Hinds |
| 8,618,400 B2 | 12/2013 | Murphy |
| 8,935,438 B1 | 1/2015 | Ivanchenko |
| 2001/0049470 A1 | 12/2001 | Mault et al. ................... 600/300 |
| 2002/0146670 A1 | 10/2002 | Selles et al. ................... 434/247 |
| 2003/0020629 A1 | 1/2003 | Swartz et al. ............. 340/825.25 |
| 2003/0040688 A1 | 2/2003 | Bauer ............................ 601/23 |
| 2003/0093012 A1 | 5/2003 | Smyser |
| 2003/0137495 A1 | 7/2003 | Canova |
| 2004/0021681 A1 | 2/2004 | Liao ............................. 345/702 |
| 2004/0058305 A1 | 3/2004 | Lurie et al. ................... 434/265 |
| 2004/0110602 A1 | 6/2004 | Feldman |
| 2004/0176226 A1 | 9/2004 | Carlson |
| 2004/0260215 A1 | 12/2004 | Kim ............................. 601/99 |
| 2005/0040999 A1 | 2/2005 | Numano ........................ 345/1.1 |
| 2005/0130742 A1 | 6/2005 | Feldman |
| 2005/0177054 A1 | 8/2005 | Yi |
| 2005/0209049 A1* | 9/2005 | Shields ............................ 482/8 |
| 2005/0219355 A1 | 10/2005 | Tahara et al. .............. 348/14.05 |
| 2005/0283204 A1 | 12/2005 | Buhlmann |
| 2006/0035762 A1 | 2/2006 | Smyser et al. ................. 482/91 |
| 2006/0064042 A1 | 3/2006 | Smyser et al. ............... 600/595 |
| 2006/0100899 A1 | 5/2006 | Tajima ............................ 705/2 |
| 2006/0122819 A1 | 6/2006 | Carmel |
| 2006/0247095 A1 | 11/2006 | Rummerfield ................... 482/1 |
| 2007/0155589 A1 | 1/2007 | Shimizu |
| 2007/0024736 A1 | 2/2007 | Matsuda |
| 2007/0051842 A1 | 3/2007 | Pryor .......................... 242/378.3 |
| 2007/0184953 A1 | 8/2007 | Luberski |
| 2007/0219059 A1 | 9/2007 | Schwartz et al. ................ 482/8 |
| 2007/0219469 A1 | 9/2007 | Vardy |
| 2007/0232455 A1 | 10/2007 | Hanoun |
| 2007/0249975 A1 | 10/2007 | Pan et al. ...................... 601/118 |
| 2007/0270727 A1 | 11/2007 | KhorassaniZadeh |
| 2008/0090703 A1 | 4/2008 | Rosenberg .................... 492/8 |
| 2008/0091762 A1 | 4/2008 | Neuhauser et al. .......... 709/201 |
| 2008/0096726 A1 | 4/2008 | Riley et al. ..................... 482/8 |
| 2008/0100718 A1 | 5/2008 | Louks et al. ................ 348/211.2 |
| 2008/0101272 A1 | 5/2008 | Hayes et al. .................. 370/313 |
| 2008/0132388 A1 | 6/2008 | Clem |
| 2008/0146336 A1 | 6/2008 | Feldman et al. ................. 463/37 |
| 2008/0161051 A1 | 7/2008 | Schobbert et al. ............ 455/558 |
| 2008/0171311 A1 | 7/2008 | Centen |
| 2008/0261696 A1 | 10/2008 | Yamazaki et al. ............... 463/39 |
| 2008/0262918 A1 | 10/2008 | Wiener ......................... 705/14 |
| 2008/0281234 A1 | 11/2008 | Goris |
| 2008/0287832 A1 | 11/2008 | Collins et al. ................ 600/587 |
| 2008/0300055 A1 | 12/2008 | Lutnick |
| 2009/0017993 A1 | 1/2009 | Khanicheh et al. ............ 482/49 |
| 2009/0025475 A1 | 1/2009 | DeBeliso et al. .......... 73/379.02 |
| 2009/0035740 A1 | 2/2009 | Reed et al. ................... 434/265 |
| 2009/0048021 A1 | 2/2009 | Lian et al. ....................... 463/37 |
| 2009/0048070 A1 | 2/2009 | Vincent et al. ................... 482/8 |
| 2009/0069160 A1 | 3/2009 | Summers ........................ 482/91 |
| 2009/0076855 A1 | 3/2009 | McCord ........................... 705/3 |
| 2009/0098980 A1 | 4/2009 | Waters |

(56) References Cited

U.S. PATENT DOCUMENTS

| | | |
|---|---|---|
| 2009/0144080 A1 | 6/2009 | Gray et al. .......... 705/2 |
| 2009/0148821 A1 | 6/2009 | Carkner et al. .......... 434/265 |
| 2009/0228068 A1 | 9/2009 | Buhlmann et al. .......... 607/48 |
| 2009/0286654 A1 | 11/2009 | Rice |
| 2010/0021876 A1 | 1/2010 | Clash .......... 434/265 |
| 2010/0265179 A1 | 1/2010 | Ram .......... 345/163 |
| 2010/0056341 A1 | 3/2010 | Ellis et al. .......... 482/9 |
| 2010/0069148 A1 | 3/2010 | Cargill .......... 463/25 |
| 2010/0087763 A1 | 4/2010 | Hane-Karr .......... 601/137 |
| 2010/0127983 A1 | 5/2010 | Irani |
| 2010/0137105 A1 | 6/2010 | McLaughlin .......... 482/8 |
| 2010/0178981 A1 | 7/2010 | Holcomb et al. .......... 463/37 |
| 2010/0197462 A1 | 8/2010 | Piane |
| 2010/0245239 A1 | 9/2010 | Sternberg |
| 2010/0248822 A1 | 9/2010 | Migos et al. .......... 463/29 |
| 2010/0255862 A1 | 10/2010 | Mitsunaga et al. .......... 455/466 |
| 2010/0255957 A1 | 10/2010 | Clem et al. .......... 482/49 |
| 2010/0259472 A1 | 10/2010 | Radivojevic |
| 2010/0273610 A1 | 10/2010 | Johnson .......... 482/9 |
| 2010/0292050 A1 | 11/2010 | DiBenedetto et al. .......... 482/9 |
| 2010/0292600 A1 | 11/2010 | DiBenedetto et al. .......... 600/520 |
| 2011/0035303 A1 | 2/2011 | Jakstadt et al. .......... 705/34 |
| 2011/0046687 A1 | 2/2011 | Naschberger .......... 607/3 |
| 2011/0086747 A1 | 4/2011 | Broderick |
| 2011/0124470 A1 | 5/2011 | Spurling et al. .......... 482/13 |
| 2011/0125866 A1 | 5/2011 | Williams .......... 709/217 |
| 2011/0143769 A1 | 6/2011 | Jones |
| 2011/0165998 A1 | 7/2011 | Lau et al. .......... 482/8 |
| 2011/0187660 A1 | 8/2011 | Hirata et al. .......... 345/173 |
| 2011/0251021 A1 | 10/2011 | Zavadsky et al. .......... 482/5 |
| 2011/0260987 A1 | 10/2011 | Zhao et al. .......... 345/173 |
| 2011/0291943 A1 | 12/2011 | Thorn et al. .......... 345/173 |
| 2011/0302694 A1 | 12/2011 | Wang |
| 2012/0047465 A1 | 2/2012 | Noda |
| 2012/0051596 A1 | 3/2012 | Darnell |
| 2012/0058861 A1 | 3/2012 | Satut |
| 2012/0066591 A1 | 3/2012 | Hackwell .......... 715/702 |
| 2012/0071732 A1 | 3/2012 | Grey et al. .......... 600/301 |
| 2012/0075236 A1 | 3/2012 | Kim |
| 2012/0077163 A1 | 3/2012 | SucarSuccar |
| 2012/0078113 A1 | 3/2012 | Whitestone |
| 2012/0088553 A1 | 4/2012 | Nunes |
| 2012/0098744 A1 | 4/2012 | Stinson |
| 2012/0108394 A1 | 5/2012 | Jones et al. .......... 482/8 |
| 2012/0112922 A1 | 5/2012 | Hillis et al. .......... 340/657 |
| 2012/0113019 A1 | 5/2012 | Anderson .......... 345/173 |
| 2012/0116550 A1 | 5/2012 | Hoffman et al. .......... 700/91 |
| 2012/0126941 A1 | 5/2012 | Coggill .......... 340/5.54 |
| 2012/0150074 A1 | 6/2012 | Yanev et al. .......... 600/587 |
| 2012/0162080 A1 | 6/2012 | Cao .......... 345/168 |
| 2012/0260220 A1 | 10/2012 | Griffin |
| 2012/0265112 A1 | 10/2012 | Chen .......... 601/115 |
| 2012/0274508 A1 | 11/2012 | Brown |
| 2012/0306782 A1 | 12/2012 | Seo et al. .......... 345/173 |
| 2013/0009907 A1 | 1/2013 | Rosenberg |
| 2013/0059696 A1 | 3/2013 | Hijmans et al. .......... 482/8 |
| 2013/0072301 A1 | 3/2013 | Mallinson |
| 2013/0076649 A1 | 3/2013 | Myers |
| 2013/0093679 A1 | 4/2013 | Dickinson |
| 2013/0106155 A1 | 5/2013 | Chang |
| 2013/0127748 A1 | 5/2013 | Vertegaal |
| 2013/0127980 A1 | 5/2013 | Haddick |
| 2013/0201316 A1 | 8/2013 | Binder |
| 2013/0212674 A1 | 8/2013 | Boger |
| 2013/0337975 A1 | 12/2013 | Yanev et al. .......... 482/8 |
| 2013/0337976 A1 | 12/2013 | Yanev et al. .......... 482/8 |
| 2013/0344919 A1 | 12/2013 | Kim |
| 2013/0345608 A1 | 12/2013 | Ehrenreich |
| 2014/0062682 A1 | 3/2014 | Birnbaum |
| 2014/0123003 A1 | 5/2014 | Song |
| 2014/0184496 A1 | 7/2014 | Gribetz |
| 2014/0317722 A1 | 10/2014 | Tartz |
| 2014/0333543 A1 | 11/2014 | Yaney et al. .......... 345/173 |
| 2014/0335494 A1 | 11/2014 | Yaney et al. .......... 434/262 |
| 2015/0015476 A1 | 1/2015 | Yaney et al. .......... 345/156 |
| 2015/0173993 A1 | 6/2015 | Walsh |

FOREIGN PATENT DOCUMENTS

| | | |
|---|---|---|
| JP | 2006345990 | 12/2006 |
| JP | 2009142333 | 7/2009 |
| JP | 2010524094 | 7/2010 |
| JP | 2013172841 | 9/2013 |
| TW | 509566 | 1/1988 |
| TW | 201000175 A | 1/2010 |
| TW | 201300098 | 1/2013 |
| TW | 201301215 | 1/2013 |
| WO | WO 2007/025382 | 3/2007 |
| WO | WO 2012/078718 | 6/2012 |
| WO | WO 2013/192071 | 12/2013 |
| WO | WO 2013/192079 | 12/2013 |
| WO | WO 2013/192084 | 12/2013 |
| WO | 2014018049 | 1/2014 |
| WO | WO 2014/182729 | 11/2014 |
| WO | WO 2014/182735 | 11/2014 |
| WO | 2015006411 | 1/2015 |
| WO | 2015006413 | 1/2015 |

OTHER PUBLICATIONS

Jovanov et al., "A Wireless Body Area Network of Intelligent Motion Sensors for Computer Assisted Physical Rehabilitation", Journal of NeuroEngineering and Rehabilitation, Mar. 1, 2005, vol. 2, No. 6, retrieved from URL: http://www.jneuroengrehab.com/content/2/1/6, retrieved on Apr. 2, 2012, 10 pages.

Halfbakery, "Computer Mouse with Pressure Sensitive Button", printed from http://www.halfbakery.com/idea/Computer_20Mouse_20with_20pressure . . . , Cord, May 10, 2005, printed Apr. 4, 2014, 3 pages.

International Search Report and Written Opinion dated Mar. 13, 2015 for corresponding International Patent Application No. PCT/US2014/037012, 9 pages.

International Search Report and Written Opinion dated Mar. 4, 2015 for corresponding International Patent Application No. PCT/US2014/037018, 9 pages.

International Search Report and Written Opinion dated Apr. 20, 2012 for corresponding International Patent Application No. PCT/US2011/063678 (7 pages).

International Search Report and Written Opinion dated Oct. 1, 2013 for corresponding International Patent Application No. PCT/US2013/046096 (10 pages).

International Search Report and Written Opinion dated Oct. 2, 2013 for corresponding International Patent Application No. PCT/US2013/046118 (10 pages).

International Search Report and Written Opinion dated Nov. 22, 2013 for corresponding International Patent Application No. PCT/US2013/046082 (7 pages).

International Search Report and Written Opinion dated Nov. 7, 2014 for corresponding International Patent Application No. PCT/US2014/045899 (7 pages).

\* cited by examiner

PERSONAL WELLNESS MANAGEMENT PLATFORM

FIELD OF THE INVENTION

The invention relates to facilitating personal wellness management via personal wellness devices and promoting personal wellness by determining and/or evaluating aspects of personal health and/or exercise.

BACKGROUND OF THE INVENTION

Apparatus used during personal exercise are typically considered either stationary or portable. Stationary apparatus may be configured to quantify various aspects of an exercise routine, such as number of repetitions, calories burnt, etc. Portable apparatus generally include much less functionality relative to larger, stationary apparatus. Neither stationary nor portable exercise apparatus typically include personal wellness management capabilities.

SUMMARY

One aspect of the invention relates to a personal wellness system configured to facilitate personal wellness management via personal wellness devices, in accordance with one or more implementations. The personal wellness system may include one or more personal wellness devices. Individual ones of the personal wellness devices may be a portable, handheld device configured to facilitate personal exercise and personal wellness management using the device. According to some implementations, information may be transferred between at least one personal wellness device and other components of the personal wellness system. Exercises performed using a personal wellness device may be tracked, which may include monitoring and/or recording personal exercises. Exercises may be tracked based on forces exerted on a personal wellness device, a location of a personal wellness device, motion of a personal wellness device, and/or other bases for tracking personal exercise. Exercise parameters may be determined based on tracked exercises. Such exercise parameters may include information associated with cardiovascular endurance, respiratory endurance, stamina, strength, flexibility, power, speed, coordination, agility, and/or balance; calories burnt or energy expended; a completion level of a prescribed exercise routine; a frequency of a particular exercise and/or exercise in general; a quantified improvement in an exercise; and/or other exercise parameters. In some implementations, the personal wellness system may facilitate automated and/or live coaching, exercise regimen design, exercise scheduling, diet program design, rehabilitation, designing and/or scheduling wellness programs integrating two or more of the aforementioned, and/or other functions associated with personal wellness management.

In addition to the personal wellness devices, the personal wellness system may include one or more of a user accessory, external resources, a personal computing platform, a personal wellness platform server, and/or other components, which may complement and/or include one or more functionalities attributed herein to the personal wellness devices. Components of the personal wellness system, such as the personal wellness devices, the personal computing platform, the personal wellness platform server, the user accessory, and/or the external resources, may be operatively linked via one or more electronic communication links.

A given personal wellness device may include one or more of a force sensor, a geo-location sensor, a motion sensor, a heart rate sensor, a blood glucose sensor, a biometric sensor, a pedometer, an electrical muscle stimulation (EMS) interface, a camera device, an actuator, a user interface, the communications apparatus, a power supply, the electronic storage, a processor, and/or other components. One or more components of the personal wellness device may be housed by one or more housing bodies. In implementations having two housing bodies, a first housing body and a second housing body may be movably coupled together by way of a coupling mechanism such that the two housing bodies are reconfigurable between an open configuration and a closed configuration. The two housing bodies may be configured to receive compressive force during personal exercise while in the closed configuration.

The force sensor may be configured to generate a force output signal that conveys information related to compressive force exerted on the personal wellness device. The geo-location sensor may be configured to generate a location output signal conveying information related to a geo-location of the personal wellness device. The motion sensor may be configured to generate a motion output signal that conveys information related to a motion and/or orientation of the personal wellness device. The heart rate sensor may be configured to generate a heart rate output signal that conveys information related to a heart rate of a user associated with the personal wellness device. The blood glucose sensor may be configured to generate a glucose output signal that conveys information related to a concentration of glucose in the blood of a user associated with the personal wellness device. The biometric sensor may be configured to generate a biometric output signal conveying information related to a biometric feature of a user. The pedometer may be configured to generate a step output signal that conveys information related to steps taken by a user carrying the personal wellness device. The electrical muscle stimulation interface may be configured to removably couple the personal wellness device with an electrode. The electrode may be configured to provide electrical muscle stimulation to a user. The camera device may be configured to capture visual data. The actuator may be configured to provide tactile feedback to a user. The communications apparatus may be configured to receive information and/or transmit information from the personal wellness device. The power supply may be configured to supply electrical power to one or more components of the personal wellness device. The electronic storage may be configured to electronically store information. The processor of the personal wellness device may be configured to execute computer program modules.

The user interface may be configured to receive information from a user and provide information to the user. As such, the user interface may include hardware and/or software to facilitate receiving information from the user and/or providing information to the user. Examples of input devices may include one or more of a touch screen, a touch pad, a keypad, a switch, an analog stick, a button, a dial, a microphone, biometric sensor, and/or other hardware configured to receive information from a user. Examples of output devices may include one or more of a display, touch screen, speakers, and/or other hardware configured to provide information to a user. According to some implementations, the user interface may be accessible by a user with the personal wellness device in an open configuration. With the personal wellness device in a closed configuration, all, some, or none of the user interface may be accessible by a user, in various implementations.

The user accessory may be configured to be physically and/or communicatively coupled with the personal wellness device. The user accessory may be configured extend exercise capabilities of the personal wellness device, provide therapy to a user of the personal wellness device, facilitate monitoring of one or more vital signs of a user of the personal wellness device, and/or extend other functionalities of the personal wellness device.

The personal computing platform may include one or more of electronic storage, at least one processor, and/or other components. The electronic storage may be configured to electronically store information. The processor may be configured to execute computer program modules. The personal computing platform may be configured to communicatively couple with the personal wellness device and/or other components of the personal wellness system. According to some implementations, the computing platform may include one or more of a personal computer, a laptop computer, a tablet computer, a Smart phone, a personal digital assistant (PDA), a gaming console, and/or other personal computing platforms.

The personal wellness platform server may include one or more of electronic storage, at least one processor, and/or other components. The electronic storage may be configured to electronically store information. The processor may be configured to execute computer program modules. The personal wellness platform server may be configured to communicatively couple with the personal wellness device and/or other components of the personal wellness system.

The processor(s) of the personal wellness device, the personal computing platform, and/or the personal wellness platform server may be configured to provide information processing capabilities in the personal wellness system. One or more of these processors may be configured to execute one or more of a device-platform communication module, an exercise tracking module, an exercise analysis module, a physical attribute module, a instruction module, a regimen design module, a exercise scheduling module, a nutrition module, a rehabilitation module, and/or other computer program modules.

The device-platform communication module may be configured to facilitate transfer of information between at least one personal wellness device and other components of the personal wellness system such as, but not limited to, the personal computing platform and/or the personal wellness platform server. According to various implementations, information transferred between a personal wellness device and other components of the personal wellness system may include one or more exercise parameters based on tracked exercises (discussed further below), assistance with one or more exercises performed using the personal wellness device, an exercise regimen, alerts associated with scheduled exercises, a diet program, a force output signal and/or information derived therefrom, a location output signal and/or information derived therefrom, a motion output signal and/or information derived therefrom, and/or other information associated with the personal wellness system. The personal wellness device may facilitate socializing and/or merchandizing.

The exercise tracking module may be configured to track exercises performed using the personal wellness device. Tracking exercises may include monitoring and/or recording personal exercises. Information associated with personal exercises performed with the personal wellness device may be recorded by electronic storage in the personal wellness system and/or other storage accessible by the personal wellness system.

According to some implementations, the exercise tracking module may be configured to track exercises based on a force output signal generated by the force sensor, a location output signal generated by the geo-location sensor, a motion output signal generated by the motion sensor, and/or other information and/or signals. By way of non-limiting illustrations, the exercise tracking module may monitor and record, based on the force output signal, one or more of a magnitude of a compressive force exerted on the personal wellness device, a duration of a compressive force exerted on the personal wellness device, a force magnitude profile as a function of time, and/or a quantity of compressive forces exerted on the personal wellness device. The exercise tracking module may monitor and record a route, distance, and/or speed traveled during exercise performed by a user of the personal wellness device based on the location output signal. The exercise tracking module may monitor and record a motion and/or orientation of a user's body part (e.g., a user's hand) connected to and/or physically coupled with (e.g., holding, strapped to, or otherwise affixed to) the personal wellness device based on the motion output signal.

In some implementations, the exercise tracking module may be configured to recognize that an exercise is being performed using the personal wellness device based on information and/or signals received from one or more components of the personal wellness device and/or modules described herein.

In some implementations, the exercise tracking module may be configured to identify a type of exercise being performed using the personal wellness device based on information and/or signals received from one or more components of the personal wellness device and/or modules described herein. Examples of types of exercises may include one or more of flexibility exercises (e.g., stretching, yoga, and/or other flexibility exercises), aerobic exercises (e.g., cycling, swimming, walking, skipping rope, rowing, running, hiking, playing tennis, and/or other aerobic exercises), anaerobic exercises (e.g., isometric training, weight training, functional training, eccentric training, sprinting, and/or other anaerobic exercises), and/or other types of exercises.

The exercise analysis module may be configured to determine one or more exercise parameters based on exercises tracked by the exercise tracking module. According to various implementations, examples of exercise parameters may include information associated with cardiovascular endurance, respiratory endurance, stamina, strength, flexibility, power, speed, coordination, agility, and/or balance; calories burnt or energy expended; a completion level of a prescribed exercise routine; a frequency of a particular exercise and/or exercise in general; a quantified improvement in an exercise; and/or other exercise parameters. In some implementations, one or more exercise parameters may be based on a comparison with tracked exercises of one or more users of other personal wellness devices. For example, the time taken to run a common route may be compared between two or more users. As another example, respective improvements in particular exercises may be compared between two or more users.

Aside from exercise, the exercise analysis module may be configured to analyze other wellness disciplines and/or a condition of a user. Such other wellness disciplines may include nutrition, relaxation, and/or other wellness disciplines. A user condition may be determined based on heart rate and/or other body measures. The exercise analysis module may be configured to provide an integrated analysis involving exercise, user condition, individual wellness disciplines, and/or other information associated with wellness.

The physical attribute module may be configured to receive physical attribute information. Examples of physical attribute information may relate to one or more of height, weight, age, gender, and/or other physical attributes. According to some implementations, physical attribute information may be received from a user by the personal wellness device via the user interface. In some implementations, the physical attribute module may be configured to automatically receive physical attribute information. For example, the personal wellness device may be used in conjunction with an accessory to function as a scale to automatically provide body weight information to the physical attribute module. The personal computing platform and/or the personal wellness platform server may receive physical attribute information from the personal wellness device via the device-platform communication module.

The instruction module may be configured to provide assistance with one or more exercises performed using the personal wellness device. Examples of assistance may include one or more of instructions, guidance, advice, coaching, and/or other assistance. The assistance may be provided by way of text, illustrations, video, sounds, speech, and/or media presented via the user interface. In some implementations, the instruction module may be configured to assist a user before, during, and/or after a given exercise is performed. The assistance provided by the instruction module may be based on one or more of a live interaction with a human trainer, nutritionist, rehabber, and/or coach; an automated response; and/or other sources of assistance with exercises.

The regimen design module may be configured to facilitate designing an exercise regimen. According to some implementations, an exercise regimen may include a plan designed to give a positive result in personal wellness. The plan may include a schedule of times to exercise, an overall duration of the regimen, particular exercises for the regimen, outcome goals, performance milestones, and/or other information associated with personal exercise. The exercise regimen may be designed manually by a user, automatically via the regimen design module, and/or by a combination of manual and automatic design. The exercise regimen, or portions thereof, may be designed automatically based on one or more of previously tracked exercises, previously determined exercise parameters, physical attributes, feedback provided by the instruction module, nutrition information, and/or other information associated with the personal wellness system.

The exercise scheduling module may be configured to monitor one or more scheduled exercises associated with a user and/or provide alerts associated with the one or more scheduled exercises. Monitoring scheduled exercises may include identifying scheduled exercises based on an exercise regimen (see, e.g., the regimen design module) and/or a calendar associated with a user. Providing an alert associated with a scheduled exercise may include sounding a tone and/or other audible sound via the personal wellness device, and/or sending the user an email, text message, reminder, voice message, and/or other communication accessible via the personal wellness device, the personal computing platform, and/or the personal wellness platform server. In some implementations, the exercise scheduling module may be configured to adjust an exercise regimen based on non-exercise elements of a calendar associated with a user. For example, if an exercise is scheduled for a given time, but a user schedules an appointment for that time, the exercise scheduling module may reschedule the exercise time to accommodate the appointment. As another example, the exercise scheduling module may be configured to adjust one or more scheduled exercises to conform with a diet program so a desired balance between caloric intake and caloric expenditure is achieved.

The nutrition module may be configured to analyze a user's diet and/or facilitate designing a diet program. A diet program may include a particular selection of food and a schedule for consuming the food selections. A diet program may be designed to achieve and/or maintain a controlled body weight. A diet program may be designed manually by a user, automatically via the nutrition module, and/or by a combination of manual and automatic design. A diet program, or portions thereof, may be designed automatically based on one or more of physical attributes, fitness and/or weight goals, diet milestones, and/or other information associated with the personal wellness system.

The rehabilitation module may be configured to provide electrical muscle stimulation treatment to a user via the electrical muscle stimulation interface. Electrical muscle stimulation treatment may include elicitation of muscle contraction using electric impulses. The impulses may mimic an action potential coming from a user's central nervous system, causing the muscles to contract. The impulses may be passed from the electrical muscle stimulation interface to an electrode operatively coupled with the electrical muscle stimulation interface. The electrode may include pads configured to adhere to a user's skin. The impulses may be delivered through the electrode on the skin in direct proximity to the muscles to be stimulated.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
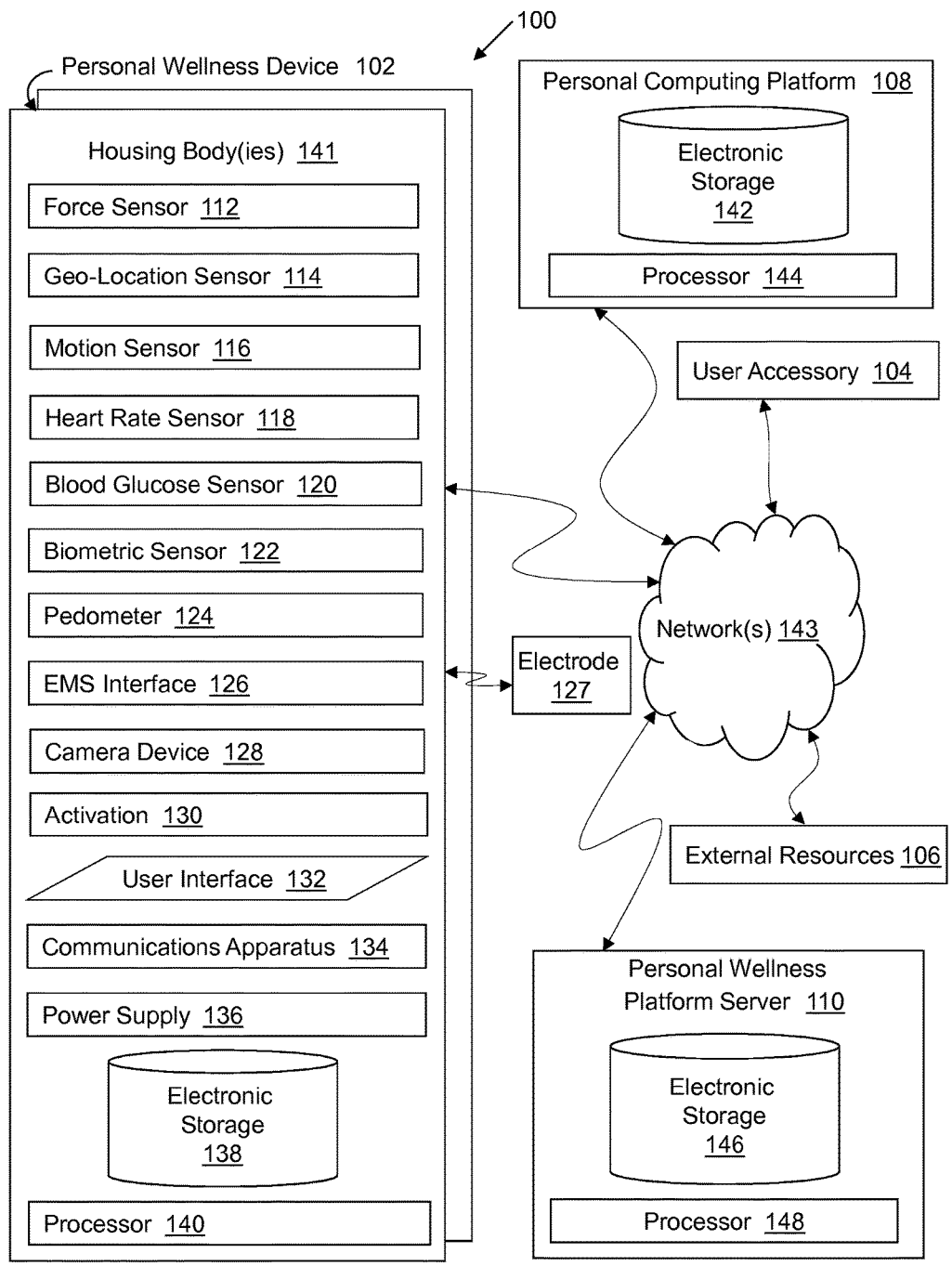
FIG. 1 illustrates a personal wellness system configured to facilitate personal wellness management via personal wellness devices, in accordance with one or more implementations.

FIG. 1 illustrates a personal wellness system 100 configured to facilitate personal wellness management via personal wellness devices, in accordance with one or more implementations. The personal wellness system 100 may include one or more personal wellness devices 102. Individual ones of the personal wellness devices 102 may be a portable, handheld device configured to facilitate personal exercise and personal wellness management using the device. According to some implementations, information may be transferred between at least one personal wellness device 102 and other components of personal wellness system 100. Exercises performed using personal wellness device 102 may be tracked, which may include monitoring and/or recording personal exercises. Exercises may be tracked based on forces exerted on personal wellness device 102, a location of personal wellness device 102, motion of personal wellness device 102, and/or other bases for tracking personal exercise. Exercise parameters may be determined based on tracked exercises. Such exercise parameters may include information associated with cardiovascular endurance, respiratory endurance, stamina, strength, flexibility, power, speed, coordination, agility, and/or balance; calories burnt or energy expended; a completion level of a prescribed exercise routine; a frequency of a particular exercise and/or exercise in general; a quantified improvement in an exercise; and/or other exercise parameters. In some implementations, personal wellness system 100 may facilitate automated and/or live coaching, exercise regimen design, exercise scheduling, diet program design, rehabilitation, designing and/or scheduling wellness programs integrating two or more of the aforementioned, and/or other functions associated with personal wellness management.

In addition to personal wellness device 102, personal wellness system 100 may include one or more of a user accessory 104, external resources 106, a personal computing platform 108, a personal wellness platform server 110, and/or other components, which may complement and/or include one or more functionalities attributed herein to personal wellness device 102. Components of personal wellness system 100, such as personal wellness device 102, personal computing platform 108, personal wellness platform server 110, user accessory 104, and/or external resources 106, may be operatively linked via one or more electronic communication links. For example, such electronic communication links may be established, at least in part, via wired or wireless network(s) 143, which may include the Internet, WiFi, LAN, ANT+, Bluetooth, low-power Bluetooth, and/or other networks. It will be appreciated that this is not intended to be limiting, and that the scope of this disclosure includes implementations in which personal wellness device 102, personal computing platform 108, personal wellness platform server 110, user accessory 104, and/or external resources 106 are operatively linked via some other communication media.

As depicted in FIG. 1, personal wellness device 102 may include one or more of a force sensor 112, a geo-location sensor 114, a motion sensor 116, a heart rate sensor 118, a blood glucose sensor 120, a biometric sensor 122, a pedometer 124, an electrical muscle stimulation (EMS) interface 126, a camera device 128, an actuator 130, a user interface 132, communications apparatus 134, a power supply 136, electronic storage 138, a processor 140, and/or other components, all housed by one or more housing body(ies) 141. According to some implementations, housing body(ies) 141 may comprise two housing bodies including a first housing body and a second housing body. The first housing body and the second housing body may be movably coupled together by way of a coupling mechanism such that the two housing bodies are reconfigurable between an open configuration and a closed configuration. The two housing bodies may be configured to receive compressive force during personal exercise while in the closed configuration. The user interface 132 may be accessible with the two housing bodies in the open configuration. Exemplary implementations of a personal wellness device having two housing bodies are described in U.S. patent application Ser. No. 13/527,465, filed on Jun. 19, 2012 and entitled "Personal Wellness Device," which is incorporated herein by reference.

The force sensor 112 may be configured to generate a force output signal that conveys information related to compressive force exerted on personal wellness device 102. Such information may include or be used to determine magnitude of force, duration of force, a force magnitude profile as a function of time, a quantity of compressive forces, and/or other information related to compressive force exerted on personal wellness device 102. The force output signal generated by force sensor 112 may be received and/or utilized by one or more modules executable by processor 140, as described further herein. By way of non-limiting example, force sensor 112 may include a FlexiForce A201 force sensor from Tekscan. However, other apparatus configured for force sensing are contemplated and within the scope of the invention.

The geo-location sensor 114 may be configured to generate a location output signal conveying information related to a geo-location of personal wellness device 102. The location output signal may be used to quantify one or more parameters of personal exercise. Such parameters may include speed, distance traveled, course of travel, and/or other parameters related to a geo-location of personal wellness device 102. By way of non-limiting example, geo-location sensor 114 may include a GPS device and/or other device configured to generate signals related to geo-location. However, other apparatus and techniques for location sensing and/or detecting are contemplated and within the scope of the invention.

The motion sensor 116 may be configured to generate a motion output signal that conveys information related to a motion and/or orientation of personal wellness device 102. The motion output signal may be used to quantify motions, changes in motion, orientation, changes in orientation, and/or information derived therefrom. By way of non-limiting example, motion sensor 116 may include an accelerometer configured to generate signals related to motion and/or orientation. However, other apparatus and techniques for motion and/or orientation sensing and/or detection are contemplated and within the scope of the invention.

The heart rate sensor 118 may be configured to generate a heart rate output signal that conveys information related to a heart rate of a user associated with personal wellness device 102. The heart rate sensor 118 may utilize electrocardiography (ECG or EKG). The heart rate output signal may be used to monitor heart rate in real time or record heart rate data for later observation and/or analysis. In some implementations, heart rate sensor 118 is integrated into personal wellness device 102 such that heart rate sensor 118 may measure a user's heart rate by way of physical contact between the user and personal wellness device 102. The heart rate sensor 118 may communicatively couple with a heart rate monitor that is separate and distinct from personal wellness device 102, according to some implementations. Examples of separate and distinct heart rate monitors may include a chest strap, a finger clip, a garment with an integrated heart rate monitor, and/or other devices configured to probe heart rate.

The blood glucose sensor 120 may be configured to generate a glucose output signal that conveys information related to a concentration of glucose in the blood of a user associated with personal wellness device 102. The glucose output signal may be used to determine a concentration of glucose and/or information derived therefrom. In some implementations, blood glucose sensor 120 may require a blood sample from a user in order to generate the glucose output signal. The blood glucose sensor 120 may be based on one or more non-invasive technologies including near IR detection, ultrasound, dielectric spectroscopy, and/or other non-invasive technologies for determining glucose concentration, in accordance with some implementations.

The biometric sensor 122 may be configured to generate a biometric output signal conveying information related to a biometric feature of a user. The biometric output signal may be used to identify and/or authenticate a user of personal wellness device 102. A biometric feature of a user may include physiological characteristics related to the shape of the body of the user. Examples of physiological characteristics may include particular geometries of a fingerprint, face, palm, hand, iris, retina, and/or other physiological characteristics. A biometric feature of a user may include deoxyribonucleic acid (DNA) associated with the user. The biometric sensor 122 may include an image capture device, a biometric scanner, and/or other device configured to observe biometric features. In some implementations, biometric sensor 122 is included in user interface 132.

The pedometer 124 may be configured to generate a step output signal that conveys information related to steps taken by a user carrying personal wellness device 102. The step output signal may be used to determine a number of steps taken, a distance traveled, and/or other information related to or derived from steps taken by a user. In some implementations, pedometer 124 may include a separate and distinct device communicatively coupled with personal wellness device 102 and configured to transmit the step output signal to personal wellness device 102.

The electrical muscle stimulation interface 126 may be configured to removably couple personal wellness device 102 with an electrode 127. The electrode 127 may be configured to provide electrical muscle stimulation to a user. In some implementations, electronic pulses (or other waveforms) may be provided by electrical muscle stimulation interface 126 to electrode 127, which in turn may deliver the electrical pulses to a surface area of a user's body causing proximate muscles to exercise passively.

The camera device 128 may be configured to capture visual data. The visual data may include still images, video, and/or other visual data. In some implementations, camera device 128 may be utilized as biometric sensor 122. The camera device 128 may include, by way of non-limiting example, a digital camera, a 2D camera, a 3D camera, and/or other imaging devices.

The actuator 130 may be configured to provide tactile feedback to a user. Tactile feedback may be preferable in some use scenarios, for example, where other feedback mechanisms such as audio or visual may be undesired. Tactile feedback may include forces, vibrations, motions, and/or other tactile feedback provided to the user. The actuator 130 may include a mechanical device configured to cause one or more motions of personal wellness device 102. In some implementations, actuator 130 may include an electric motor with an unbalanced mass on its driveshaft such that rotation of the driveshaft generates vibrations. One or more parameters of the tactile feedback may be varied to convey different information to a user. The parameters may include one or more of direction, source location, duration, frequency, amplitude, and/or other parameters.

The user interface 132 may be configured to receive information from a user and provide information to the user. As such, user interface 132 may include hardware and/or software to facilitate receiving information from the user and/or providing information to the user. Examples of input devices may include one or more of a touch screen, a touch pad, a keypad, a switch, an analog stick, a button, a dial, a microphone, biometric sensor, and/or other hardware configured to receive information from a user. Examples of output devices may include one or more of a display, touch screen, speakers, and/or other hardware configured to provide information to a user.

In some implementations, user interface 132 may be configured to present user configurable settings to the user. The user interface 132 may be configured to receive selections from the user of values for the user configurable settings. One or more user configurable settings may impact the current activity of one or more components of personal wellness device 102. By way of non-limiting example, the user configurable settings may activate and/or deactivate one or more components of personal wellness device 102, and/or may configure one or more aspects of operation of personal wellness device 102. The user configurable settings may be related to personal exercise and/or wellness of a user of personal wellness device 102. The user configurable settings may be provided to processor 140 of personal wellness device 102. The user configurable settings may be provided to one or more processors of user accessory 104, personal computing platform 108, personal wellness platform server 110, and/or other components of personal wellness system 100.

The communications apparatus 134 may be configured to receive information and/or transmit information from personal wellness device 102. As such, communications apparatus 134 may include one or both of a wireless communications interface or a wired communications interface. Examples of a communications interface may include a wired or wireless transmitter, a wired or wireless receiver, and/or a combined wired or wireless transmitter and receiver. The communications apparatus 134 may be configured to communicatively couple personal wellness device 102 with a computing platform (e.g., personal computing platform 108 and/or personal wellness platform server 110) configured to receive and process information related to compressive force exerted on the two housing bodies, a user accessory that is separate and distinct from personal wellness device 102, and/or other components of personal wellness system 100.

The power supply 136 may be configured to supply electrical power to one or more components of personal wellness device 102. By way of non-limiting example, power supply 136 may include one or more of a battery, a capacitor, apparatus for receiving electrical power from an external source (e.g., a wall socket), and/or other power supplies. In some implementations, power supply 136 may be rechargeable. In one implementation, where communications apparatus 134 includes a USB port or other wired communications port, communications apparatus 134 may receive electrical power from a component of personal wellness system 100 and/or another source to recharge power supply 136.

The electronic storage 138 may be configured to electronically store information. Exemplary implementations of electronic storage that is the same or similar to electronic storage 138 are described further herein.

The processor 140 may be configured to execute computer program modules. Exemplary implementations of processors that are the same or similar to processor 140 are described in connection with FIG. 2.

The user accessory 104 may be configured to be physically and/or communicatively coupled with personal wellness device 102. The user accessory 104 may be configured extend exercise capabilities of personal wellness device 102, provide therapy to a user of personal wellness device 102, facilitate monitoring of one or more vital signs of a user of personal wellness device 102, and/or extend other functionalities of personal wellness device 102.

In implementations where user accessory 104 is configured to extend exercise capabilities of personal wellness device 102, user accessory 104 may include a strap (not depicted in FIG. 1) or other apparatus configured for similar functionality attributed herein to the strap. Such a strap may be configured to physically couple to personal wellness device 102 and facilitate exertion of compressive force on personal wellness device 102 responsive to a tensive force exerted on the strap. The strap may be removably coupled to personal wellness device 102 by hooks, snaps, hook and loop fasteners, and/or other means for removable coupling.

In implementations where user accessory 104 is configured to provide therapy to a user of personal wellness device 102, user accessory 104 may include electrode 127. In some implementations, electrical muscle stimulation interface 126 may be configured to removably couple personal wellness device 102 with electrode 127. The electrode 127 may be configured to provide electrical muscle stimulation to a user.

In implementations where user accessory 104 is configured to facilitate monitoring of one or more vital signs of a user of personal wellness device 102, user accessory 104 may include one or more accessories configured to facilitate monitoring of one or more of body temperature, heart rate, respiration rate, blood pressure, body sweat, and/or other vital signs. In some implementations, user accessory 104 may include a chest strap, a finger clip, a garment with an integrated heart rate monitor, and/or other devices configured to probe heart rate, which may communicatively couple with heart rate sensor 118. In some implementations, user accessory 104 may include a blood pressure sensor. The blood pressure sensor may be configured to generate a blood pressure output signal that conveys information related to a blood pressure of a user associated with personal wellness device 102.

In implementations where user accessory 104 is configured to extend other functionalities of personal wellness device 102, user accessory 104 may include one or more of a wired headset; a wireless headset; wired headphones; wireless headphones; a device that includes a display; one or more sensors configured to be attached to a user's body and provide a signal conveying information associated with motion, position, and/or other information associated with a user; a device configured to determine user and/or body part motion, size, and/or position (e.g., MS Kinect™); and/or other accessories configured to extend one or more functionalities of personal wellness device 102. A device configured to determine user and/or body part motion, size, and/or position may perform such determination(s) based on optical information, signals received from one or more sensors attached to a user's body, and/or other information associated with user.

The external resources 106 may include sources of information, hosts and/or providers of personal wellness systems, external entities participating with personal wellness system 100, and/or other resources. According to some implementations, external resources 106 may include doctor-specific software, hospital contact management system (CMS), corporate CMS, and/or other resources. In some implementations, some or all of the functionality attributed herein to external resources 106 may be provided by resources included in personal wellness system 100.

The personal computing platform 108 may include one or more of electronic storage 142, at least one processor 144, and/or other components. The electronic storage 142 may be configured to electronically store information. Exemplary implementations of electronic storage that is the same or similar to electronic storage 142 are described further herein. The processor 144 may be configured to execute computer program modules. Exemplary implementations of processors that are the same or similar to processor 144 are described in connection with FIG. 2. The personal computing platform 108 may be configured to communicatively couple with personal wellness device 102 and/or other components of personal wellness system 100. The personal computing platform 108 may be configured to receive, transmit, process, and/or store information related to one or more of personal exercise, compressive force exerted on personal wellness device 102, and/or other information associated with personal wellness system 100. According to some implementations, the computing platform 104 may include one or more of a personal computer, a laptop computer, a tablet computer, a Smart phone, a personal digital assistant (PDA), a gaming console, and/or other personal computing platforms.

The personal wellness platform server 110 may include one or more of electronic storage 146, at least one processor 148, and/or other components. The electronic storage 146 may be configured to electronically store information. Exemplary implementations of electronic storage that is the same or similar to electronic storage 146 are described further herein. The processor 148 may be configured to execute computer program modules. Exemplary implementations of processors that are the same or similar to processor 146 are described in connection with FIG. 2. The personal wellness platform server 110 may be configured to communicatively couple with personal wellness device 102 and/or other components of personal wellness system 100. The personal wellness platform server 110 may be configured to receive, transmit, process, and/or store information related to one or more of personal exercise, compressive force exerted on personal wellness device 102, and/or other information associated with personal wellness system 100. In some implementations, personal wellness platform server 110 may be implemented by a cloud of computing platforms operating together as personal wellness platform server 110.

Electronic storage 138 of personal wellness device 102, electronic storage 142 of personal computing platform 108, and/or electronic storage 146 of personal wellness platform server 110 may comprise electronic storage media that electronically stores information. Such electronic storage media may include one or both of system storage that is provided integrally (i.e., substantially non-removable) with personal wellness device 102, personal computing platform 108, and/or personal wellness platform server 110. Electronic storage media may include removable storage that is removably connectable to personal wellness device 102, personal computing platform 108, and/or personal wellness platform server 110 via, for example, a port (e.g., a USB port, a firewire port, etc.) or a drive (e.g., a disk drive, etc.). Electronic storage 138, electronic storage 142, and/or electronic storage 146 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 138, electronic storage 142, and/or electronic storage 146 may include one or more virtual storage resources (e.g., cloud storage, a virtual private network, and/or other virtual storage resources). Electronic storage 138, electronic storage 142, and/or electronic storage 146 may store software algorithms; information determined by one or more processors (e.g., processor 140, processor 144, and/or processor 148); information received from personal wellness device 102, user accessory 104, external resources 106, personal computing platform 108, and/or personal wellness platform server 110; and/or other information that enables personal wellness system 100 to function as described herein.

Figure 2:
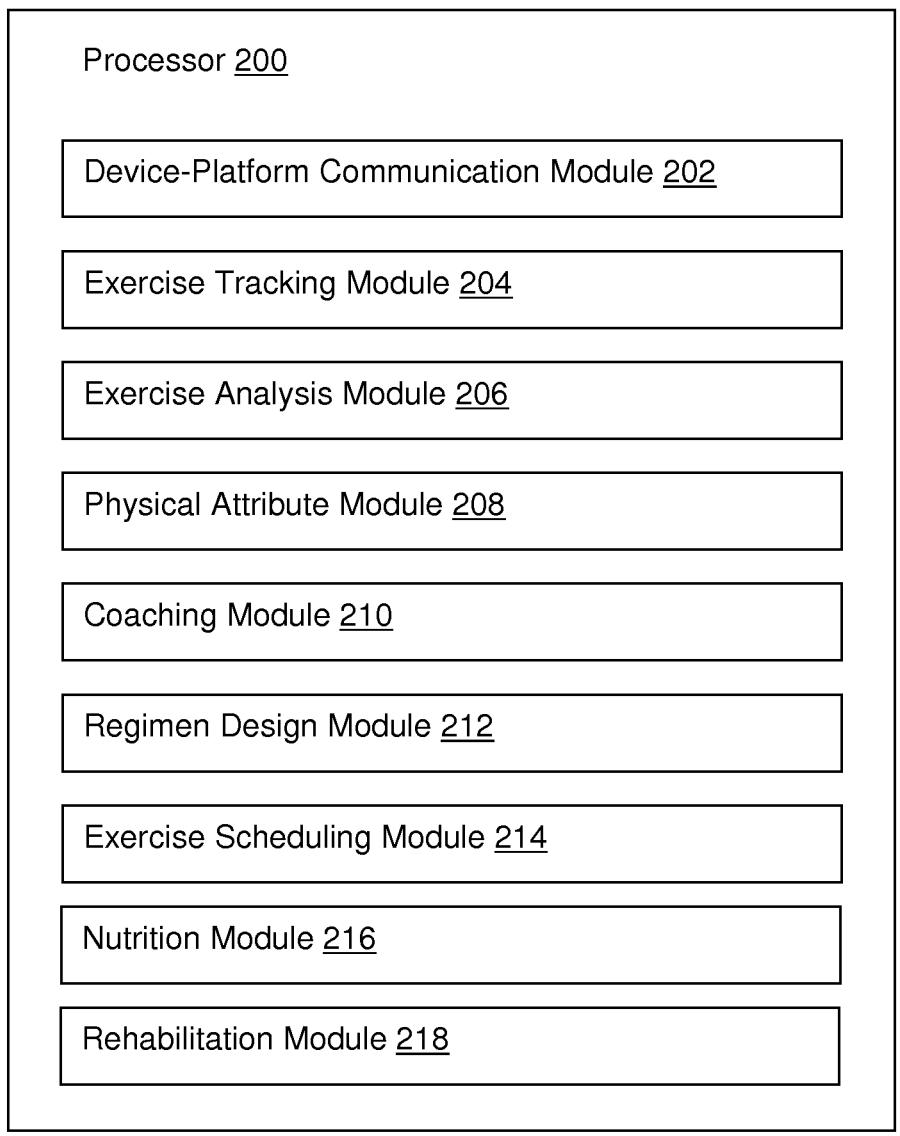
FIG. 2 illustrates an exemplary processor included in one or more components of the personal wellness system, in accordance with one or more implementations.

FIG. 2 illustrates an exemplary processor 200 included in one or more components of personal wellness system 100, in accordance with one or more implementations. The processor 200 may be the same or similar to processor 140 of personal wellness device 102, processor 144 of personal computing platform 108, and/or processor 148 of personal wellness platform server 110. Processor 200 is configured to provide information processing capabilities in personal wellness system 100. As such, processor 200 may include one or more of a digital processor, an analog processor, a digital circuit designed to process information, an analog circuit designed to process information, a state machine, and/or other mechanisms for electronically processing information. Although processor 200 is shown in FIG. 2 as a single entity, this is for illustrative purposes only. In some implementations, processor 200 may include a plurality of processing units. These processing units may be physically located within the same device, or processor 200 may represent processing functionality of a plurality of devices operating in coordination.

As depicted in FIG. 2, processor 200 may be configured to execute one or more of a device-platform communication module 202, an exercise tracking module 204, an exercise analysis module 206, a physical attribute module 208, a instruction module 210, a regimen design module 212, a exercise scheduling module 214, a nutrition module 216, a rehabilitation module 218, and/or other computer program modules. Processor 200 may be configured to execute modules 202, 204, 206, 208, 210, 212, 214, 216, 218, and/or other modules by software; hardware; firmware; some combination of software, hardware, and/or firmware; and/or other mechanisms for configuring processing capabilities on processor 200.

It should be appreciated that although modules 202, 204, 206, 208, 210, 212, 214, 216, and 218 are illustrated in FIG. 2 as being co-located within a single processing unit, in implementations in which processor 200 includes multiple processing units, one or more of modules 202, 204, 206, 208, 210, 212, 214, 216, and/or 218 may be located remotely from the other modules. For example, one or more of modules 202, 204, 206, 208, 210, 212, 214, 216, 218, and/or other modules may be executed by processor 140 of personal wellness device 102, processor 144 of personal computing platform 108, and/or processor 148 of personal wellness platform server 110. The description of the functionality provided by the different modules 202, 204, 206, 208, 210, 212, 214, 216, and/or 218 described below is for illustrative purposes, and is not intended to be limiting, as any of modules 202, 204, 206, 208, 210, 212, 214, 216, and/or 218 may provide more or less functionality than is described. For example, one or more of modules 202, 204, 206, 208, 210, 212, 214, 216, and/or 218 may be eliminated, and some or all of its functionality may be provided by other ones of modules 202, 204, 206, 208, 210, 212, 214, 216, and/or 218. As another example, processor 200 may be configured to execute one or more additional modules that may perform some or all of the functionality attributed below to one of modules 202, 204, 206, 208, 210, 212, 214, 216, and/or 218.

The device-platform communication module 202 may be configured to facilitate transfer of information between at least one personal wellness device 102 and other components of personal wellness system 100 such as, but not limited to, personal computing platform 108 and/or personal wellness platform server 110. According to various implementations, information transferred between personal wellness device 102 and other components of personal wellness system 100 may include one or more exercise parameters based on tracked exercises (discussed further below), assistance with one or more exercises performed using personal wellness device 102, an exercise regimen, alerts associated with scheduled exercises, a diet program, a force output signal and/or information derived therefrom, a location output signal and/or information derived therefrom, a motion output signal and/or information derived therefrom, and/or other information associated with personal wellness system 100. In some implementations, device-platform communication module 202 may be configured to facilitate communication between one or more other devices carried by the user. For example, device-platform communication module 202 may communicate with a pacemaker installed in a user to adjust its settings. The personal wellness device 102 may facilitate socializing and/or merchandizing, according to some implementations, as described in U.S. patent application Ser. No. 13/527,437, filed on Jun. 19, 2012, and entitled "Merchandizing, Socializing, and/or Gaming Via a Personal Wellness Device and/or a Personal Wellness Platform," which is incorporated herein by reference.

The exercise tracking module 204 may be configured to track exercises performed using personal wellness device 102. Tracking exercises may include monitoring and/or recording personal exercises. Personal exercises may include traditional forms of exercise and/or everyday activities. Everyday activities may include cleaning, watching TV, mowing, and/or other everyday activities. Information associated with personal exercises performed with personal wellness device 102 may be recorded by electronic storage 138, electronic storage 142, electronic storage 146, and/or other storage accessible by personal wellness system 100.

According to some implementations, exercise tracking module 204 may be configured to track exercises based on a force output signal generated by force sensor 112, a location output signal generated by geo-location sensor 114, a motion output signal generated by motion sensor 116, information received from an accessory such as a device configured to optically determine user and/or body part motion and/or position, and/or other information and/or signals. By way of non-limiting illustrations, exercise tracking module 204 may monitor and record, based on the force output signal, one or more of a magnitude of a compressive force exerted on personal wellness device 102, a duration of a compressive force exerted on personal wellness device 102, a force magnitude profile as a function of time, and/or a quantity of compressive forces exerted on personal wellness device 102. The exercise tracking module 204 may monitor and record a route, distance, and/or speed traveled during exercise performed by a user of personal wellness device 102 based on the location output signal. The exercise tracking module 204 may monitor and record a motion and/or orientation of a user's body part (e.g., a user's hand) connected to and/or physically coupled with (e.g., holding, strapped to, or otherwise affixed to) personal wellness device 102 based on the motion output signal.

In some implementations, exercise tracking module 204 may be configured to recognize that an exercise is being performed using personal wellness device 102 based on information and/or signals received from one or more components of personal wellness device 102 and/or modules described in connection with processor 200.

In some implementations, exercise tracking module 204 may be configured to identify a type of exercise being performed using personal wellness device 102 based on information and/or signals received from one or more components of personal wellness device 102 and/or modules described in connection with processor 200. Examples of types of exercises may include one or more of flexibility exercises (e.g., stretching, yoga, and/or other flexibility exercises), aerobic exercises (e.g., cycling, swimming, walking, skipping rope, rowing, running, hiking, playing tennis, and/or other aerobic exercises), anaerobic exercises (e.g., isometric training, weight training, functional training, eccentric training, sprinting, and/or other anaerobic exercises), and/or other types of exercises.

The exercise analysis module 206 may be configured to determine one or more exercise parameters based on exercises tracked by exercise tracking module 204. According to various implementations, examples of exercise parameters may include information associated with cardiovascular endurance, respiratory endurance, stamina, strength, flexibility, power, speed, coordination, agility, and/or balance; calories burnt or energy expended; a completion level of a prescribed exercise routine; a frequency of a particular exercise and/or exercise in general; a quantified improvement in an exercise; and/or other exercise parameters. In some implementations, one or more exercise parameters may be based on a comparison with tracked exercises of one or more users of other personal wellness devices. For example, the time taken to run a common route may be compared between two or more users. As another example, respective improvements in particular exercises may be compared between two or more users.

Aside from exercise, exercise analysis module 206 may be configured to analyze other wellness disciplines and/or a condition of a user. Such other wellness disciplines may include nutrition, relaxation, and/or other wellness disciplines. A user condition may be determined based on heart rate and/or other body measures. The exercise analysis module may be configured to provide an integrated analysis involving exercise, user condition, individual wellness disciplines, nutrition, and/or other information associated with wellness.

The physical attribute module 208 may be configured to receive physical attribute information. Examples of physical attribute information may relate to one or more of height, weight, age, gender, and/or other physical attributes. According to some implementations, physical attribute information may be received from a user by personal wellness device 102 via user interface 132. In some implementations, physical attribute module 208 may be configured to automatically receive physical attribute information. For example, personal wellness device 102 may be used in conjunction with an accessory to function as a scale to automatically provide body weight information to physical attribute module 208. The personal computing platform 108 and/or personal wellness platform server 110 may receive physical attribute information from personal wellness device 102 via device-platform communication module 202.

The instruction module 210 may be configured to provide assistance with one or more exercises performed using personal wellness device 102. Examples of assistance may include one or more of instructions, guidance, advice, coaching, and/or other assistance. The assistance may be provided by way of text, illustrations, video, sounds, speech, and/or media presented via user interface 132. In some implementations, instruction module 210 may be configured to assist a user before, during, and/or after a given exercise is performed. The assistance provided by instruction module 210 may be based on one or more of a live interaction with a human trainer, nutritionist, rehabber, and/or coach; an automated response; and/or other sources of assistance with exercises.

The regimen design module 212 may be configured to facilitate designing an exercise regimen. According to some implementations, an exercise regimen may include a plan designed to give a positive result in personal wellness. The plan may include a schedule of times to exercise, an overall duration of the regimen, particular exercises for the regimen, outcome goals, performance milestones, and/or other information associated with personal exercise. The exercise regimen may be designed manually by a user, automatically via regimen design module 212, and/or by a combination of manual and automatic design. The exercise regimen, or portions thereof, may be designed automatically based on one or more of previously tracked exercises, previously determined exercise parameters, physical attributes, feedback provided by instruction module 210, nutrition information, user-defined restrictions and/or goals, and/or other information associated with personal wellness system 100.

The exercise scheduling module 214 may be configured to monitor one or more scheduled exercises associated with a user and/or provide alerts associated with the one or more scheduled exercises. Monitoring scheduled exercises may include identifying scheduled exercises based on an exercise regimen (see, e.g., regimen design module 212) and/or a calendar associated with a user. Providing an alert associated with a scheduled exercise may include sounding a tone and/or other audible sound via personal wellness device 102, and/or sending the user an email, text message, reminder, voice message, and/or other communication accessible via personal wellness device 102, personal computing platform 108, and/or personal wellness platform server 110. In some implementations, exercise scheduling module 214 may be configured to adjust an exercise regimen based on non-exercise elements of a calendar associated with a user. For example, if an exercise is scheduled for a given time, but a user schedules an appointment for that time, the exercise scheduling module 214 may reschedule the exercise time to accommodate the appointment. As another example, exercise scheduling module 214 may be configured to adjust one or more scheduled exercises to conform with a diet program so a desired balance between caloric intake and caloric expenditure is achieved.

The nutrition module 216 may be configured to analyze a user's diet and/or facilitate designing a diet program. A diet program may include a particular selection of food and a schedule for consuming the food selections. A diet program may be designed to achieve and/or maintain a controlled body weight. A diet program may be designed manually by a user, automatically via nutrition module 216, and/or by a combination of manual and automatic design. A diet program, or portions thereof, may be designed automatically based on one or more of physical attributes, fitness and/or weight goals, diet milestones, and/or other information associated with personal wellness system 100.

The rehabilitation module 218 may be configured to provide electrical muscle stimulation treatment to a user via electrical muscle stimulation interface 126. Electrical muscle stimulation treatment may include elicitation of muscle contraction using electric impulses. The impulses may mimic an action potential coming from a user's central nervous system, causing the muscles to contract. The impulses may be passed from electrical muscle stimulation interface 126 to electrode 127 operatively coupled with electrical muscle stimulation interface 126. The electrode 127 may include pads configured to adhere to a user's skin. The impulses may be delivered through electrode 127 on the skin in direct proximity to the muscles to be stimulated.

Figure 3:
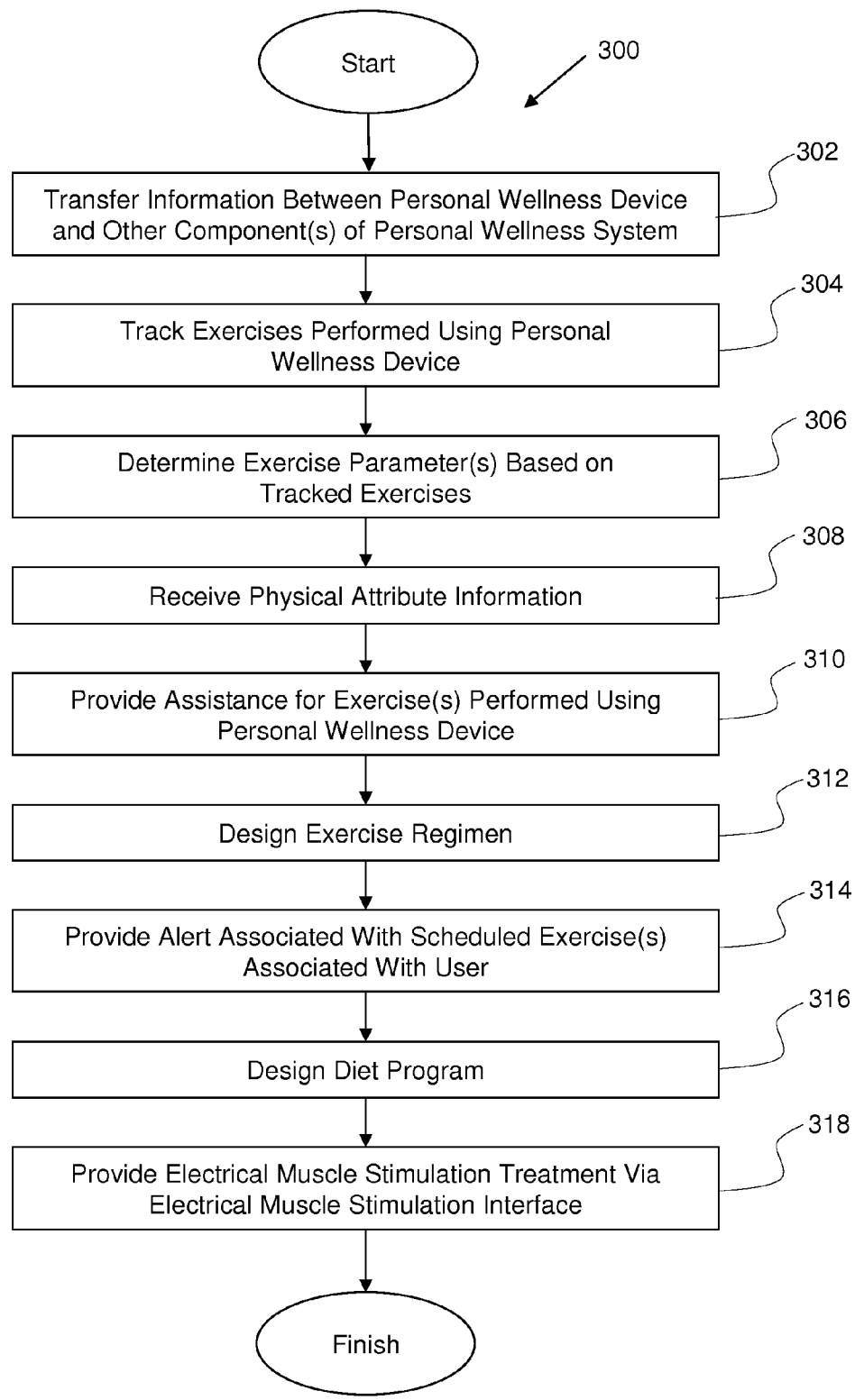
FIG. 3 illustrates a method for facilitating personal wellness management via personal wellness devices, in accordance with one or more implementations.

FIG. 3 illustrates a method 300 for facilitating personal wellness management via personal wellness devices, in accordance with one or more implementations. The operations of method 300 presented below are intended to be illustrative. In some implementations, method 300 may be accomplished with one or more additional operations not described, and/or without one or more of the operations discussed. Additionally, the order in which the operations of method 300 are illustrated in FIG. 3 and described below is not intended to be limiting.

In some implementations, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, information may be transferred between personal wellness device 102 and other components of personal wellness system 100 such as, but not limited to, personal computing platform 108 and/or personal wellness platform server 110. Operation 302 may be performed by a device-platform communication module that is the same or similar to device-platform communication module 202, in accordance with one or more implementations.

At an operation 304, exercises performed using personal wellness device 102 may be tracked. Operation 304 may be performed by an exercise tracking module that is the same or similar to exercise tracking module 204, in accordance with one or more implementations.

At an operation 306, one or more exercise parameters may be determined based on tracked exercises. Operation 306 may be performed by an exercise analysis module that is the same or similar to exercise analysis module 206, in accordance with one or more implementations.

At an operation 308, physical attribute information may be received. Operation 308 may be performed by a physical attribute module that is the same or similar to physical attribute module 208, in accordance with one or more implementations.

At an operation 310, assistance may be provided for one or more exercises performed using personal wellness device 102. Operation 310 may be performed by a instruction module that is the same or similar to instruction module 210, in accordance with one or more implementations.

At an operation 312, an exercise regimen may be designed. Operation 312 may be performed by a regimen design module that is the same or similar to regimen design module 212, in accordance with one or more implementations.

At an operation 314, an alert associated with one or more scheduled exercises associated with a user may be provided. Operation 314 may be performed by an exercise scheduling module that is the same or similar to exercise scheduling module 214, in accordance with one or more implementations.

At an operation 316, a diet program may be designed. Operation 316 may be performed by a nutrition module that is the same or similar to nutrition module 216, in accordance with one or more implementations.

At an operation 318, an electrical muscle stimulation treatment may be provided to a user via electrical muscle stimulation interface 126. Operation 318 may be performed by a rehabilitation module that is the same or similar to rehabilitation module 218, in accordance with one or more implementations.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A personal wellness device configured to facilitate personal wellness management, the personal wellness device comprising:

at least one housing body configured to receive compressive forces from a user, the compressive forces being received during one or more personal exercises performed by the user;

a force sensor configured to provide a force output signal conveying information related to the compressive forces exerted on the at least one housing body by the user during the one or more exercises, the force sensor being housed by the at least one housing body;

a motion sensor configured to provide a motion output signal conveying information related to motions experienced by the personal wellness device during the one or more exercises, the motion sensor being housed by the at least one housing body;

a user interface configured to receive information from the user and provide information to the user, the user interface being housed by the at least one housing body; and one or more physical processors configured by machine-readable instructions, the one or more physical processors being housed by the at least one housing body, the machine-readable instructions when executed causing the one or more physical processors to:

obtain the force output signal provided by the force sensor via a physical link that communicatively couples the force sensor with the one or more physical processors;

based on the information conveyed by the force output signal, determine a magnitude and/or duration of individual compressive forces exerted on the at least one housing body by the user during the one or more exercises;

obtain the motion output signal provided by the motion sensor via a data link that communicatively couples the motion sensor with the one or more physical processors;

based on the information conveyed by the motion output signal, determine individual motions experienced by the personal wellness device during the one or more exercises; and utilize (1) the determined magnitude and/or duration of the individual compressive forces exerted on the at least one housing body, (2) the determined individual motions experienced by the personal wellness device, and (3) information from previously tracked exercises in order to identify a type of exercise that corresponds to individual ones of the one or more exercises performed by the user using the personal wellness device;

determine one or more exercise parameters based on (1) the determined magnitude and/or duration of the individual compressive forces exerted and (2) the identified type of exercise corresponding to individual ones of one or more exercises; and effectuate presentation of individual ones of the one or more exercise parameters via the user interface.

2. The personal wellness device of claim 1, wherein the one or more physical processors are further configured by machine-readable instructions to receive physical attribute information from the user through user entry and/or selection via the user interface, the physical attribute information relating to one or more of height, weight, age, or gender.

3. The personal wellness device of claim 1, wherein the one or more physical processors are further configured by machine-readable instructions to provide assistance to the user via the user interface, the assistance being associated with the one or more exercises performed by the user while using the personal wellness device, the assistance including one or more of instructions, guidance, advice, or coaching provided by way of text, illustrations, video, sounds, speech, and/or media presented via the user interface.

4. The personal wellness device of claim 3, wherein the one or more physical processors are further configured by machine-readable instructions such that the assistance provided to the user via the user interface includes one or both of (1) information provided by a live interaction with a human coach in communication with the personal wellness device or (2) a predetermined instruction that is stored by the personal wellness device or that is stored at a location accessible by the personal wellness device.

5. The personal wellness device of claim 1, wherein the one or more physical processors are further configured by machine-readable instructions to facilitate designing an exercise regimen based on the identified one or more exercises and/or the determined one or more exercise parameters, the exercise regimen including a plan designed to give a positive result in personal wellness, the plan including a schedule of times to exercise and particular exercises for the exercise regimen, one or more aspects of the exercise regimen being designed manually by the user and/or automatically.

6. The personal wellness device of claim 1, wherein the one or more physical processors are further configured by machine-readable instructions to:

obtain a schedule of exercises associated with the user, the schedule of exercises including one or more scheduled exercises, the schedule of exercises being stored by the personal wellness device or at a location accessible by the personal wellness device;

identify individual ones of the one or more scheduled exercises included in the schedule of exercises; and effectuate communication of alerts to the user via the user interface of the personal wellness device, the alerts being associated with the identified scheduled exercises.

7. The personal wellness device of claim 1, wherein the one or more physical processors are configured by machine-readable instructions to:

analyze a user's diet based on the user's consumption of food, the user's consumption of food being determined based on user selections of food received via the user interface of the personal wellness device; and design a diet program based on the analyzed user's diet, the diet program including particular selections of food and a schedule for consuming the food selections, the diet program being designed to achieve and/or maintain a controlled body weight.

8. The personal wellness device of claim 1, wherein the at least one housing body comprises two housing bodies including a first housing body and a second housing body, the first housing body and the second housing body being movably coupled together by way of a coupling mechanism such that the two housing bodies are reconfigurable between an open configuration and a closed configuration, the two housing bodies being configured to receive compressive force during personal exercise while in the closed configuration, and wherein the user interface is accessible with the two housing bodies in the open configuration.

9. A personal wellness platform configured to facilitate personal wellness management via personal wellness devices, individual ones of the personal wellness devices comprising a force sensor configured to generate a force output signal conveying information relating to a compressive force exerted thereon by a user performing one or more personal exercises and a user interface configured to receive information from the user and provide information to the user, the personal wellness platform comprising:

one or more physical processors configured by machine-readable instructions to:

effectuate transfer of information via a communication link between the personal wellness platform and individual ones of the personal wellness devices, the information being associated with (1) a magnitude and/or duration of individual compressive forces exerted on individual ones of the personal wellness devices and (2) individual motions experienced by individual ones of the personal wellness devices;

utilize (1) the magnitude and/or duration of the individual compressive forces exerted on individual ones of the personal wellness devices, (2) the individual motions experienced by individual ones of the personal wellness devices and (3) information from previously tracked exercises in order to identify types of exercises performed by individual users using individual ones of the personal wellness device based on information transferred between the personal wellness platform and individual ones of the personal wellness devices;

determine one or more exercise parameters based on (1) the magnitude and/or duration of the individual compressive forces exerted and (2) the identified types of exercises; and effectuate presentation of individual ones of the one or more exercise parameters via individual ones of the personal wellness devices.

10. The personal wellness platform of claim 9, wherein the one or more physical processors are further configured by machine-readable instructions to receive physical attribute information associated with individual users of the personal wellness devices, the physical attribute information being received via entry and/or selection performed by the individual users via user interfaces of individual ones of the personal wellness devices, the physical attribute information relating to one or more of height, weight, age, DNA, or gender of the individual users.

11. The personal wellness platform of claim 9, wherein the one or more physical processors are configured by machine-readable instructions to provide assistance to the individual users via the user interfaces, the assistance being associated with the one or more exercises performed by the individual users using individual ones of the personal wellness devices, the assistance including one or more of instructions, guidance, advice, or coaching provided by way of text, illustrations, video, sounds, speech, and/or media presented via the user interfaces.

12. The personal wellness platform of claim 11, wherein the assistance provided to the individual users via the user interfaces includes one or both of (1) information provided by a live interaction with a human coach in communication with the personal wellness device or (2) a predetermined instruction that is stored by individual ones of the personal wellness devices or that is stored at a location accessible by individual ones of the personal wellness devices.

13. The personal wellness platform of claim 9, wherein the one or more physical processors are further configured by machine-readable instructions to facilitate designing an exercise regimen based on the identified exercises and/or the determined one or more exercise parameters, the exercise regimen including a plan designed to give a positive result in personal wellness, the plan including a schedule of times to exercise and particular exercises for the exercise regimen, one or more aspects of the exercise regimen being designed manually by the user and/or automatically.

14. The personal wellness platform of claim 9, wherein the one or more physical processors are further configured by machine-readable instructions to:
  obtain a schedule of exercises associated with a first user, the schedule of exercises including one or more scheduled exercises, the schedule of exercises being stored by a personal wellness device associated with the first user or at a location accessible by the personal wellness device associated with the first user;
  identify individual ones of the one or more scheduled exercises included m the schedule of exercises; and
  effectuate communication of alerts to the first user via a user interface of the personal wellness device associated with the first user, the alerts being associated with the identified one or more scheduled exercises.

15. The personal wellness platform of claim 9, wherein the one or more physical processors are further configured by machine-readable instructions to:
  analyze a first user's diet based on the first user's consumption of food, the first user's consumption of food being determined based on user selections of food received via a user interface of a personal wellness device associated with the first user; and
  design a diet program based on the analyzed first user's diet, the diet program including particular selections of food and a schedule for consuming the food selections, the diet program being designed to achieve and/or maintain a controlled body weight.

16. The personal wellness platform of claim 9, wherein the one or more physical processors are further configured by machine-readable instructions to effectuate transmission, via one or more communication links, of information from the personal wellness platform to individual ones of the personal wellness devices, the information including one or more of:
  the one or more exercise parameters determined based on the identified exercises; instruction associated with performing the one or more exercises using individual ones of the personal wellness devices;
  an exercise regime;
  alerts associated with scheduled exercises included in a schedule of exercises; or
a diet program determined from a selection of foods associated with the individual users' consumption of food.

17. The personal wellness platform of claim 9, wherein individual ones of the personal wellness devices each comprise two housing bodies including a first housing body and a second housing body, the first housing body and the second housing body being movably coupled together by way of a coupling mechanism such that the two housing bodies are reconfigurable between an open configuration and a closed configuration, the two housing bodies being configured to receive compressive force during personal exercise while in the closed configuration, one or both of the two housing bodies being configured to house one or more of the force sensor, the user interface, or one or more physical processors configured by machine-readable instructions.

* * * * *